(12) United States Patent
Ferree

(10) Patent No.: US 7,857,855 B2
(45) Date of Patent: Dec. 28, 2010

(54) DEVICES USED TO TREAT DISC HERNIATION AND ATTACHMENT MECHANISMS THEREFORE

(76) Inventor: Bret A. Ferree, 1238 Cliff Laine Dr., Cincinnati, OH (US) 45208

(*) Notice: Subject to any disclaimer, the term of this patent is extended or adjusted under 35 U.S.C. 154(b) by 291 days.

(21) Appl. No.: 12/122,612

(22) Filed: May 16, 2008

(65) Prior Publication Data

US 2008/0243256 A1    Oct. 2, 2008

Related U.S. Application Data

(63) Continuation of application No. 10/185,284, filed on Jun. 26, 2002, now abandoned, which is a continuation-in-part of application No. 09/415,382, filed on Oct. 8, 1999, now Pat. No. 6,419,704.

(51) Int. Cl.
*A61F 2/44* (2006.01)
(52) U.S. Cl. .................................. 623/17.11
(58) Field of Classification Search ............. 623/17.11, 623/17.12, 17.13, 17.16; 606/246, 279, 151
See application file for complete search history.

(56) References Cited

U.S. PATENT DOCUMENTS

| | | |
|---|---|---|
| 4,413,359 A | 11/1983 | Akiyama |
| 4,512,338 A | 4/1985 | Balko |
| 4,599,086 A | 7/1986 | Doty |
| 4,636,217 A | 1/1987 | Ogilvie |
| 4,663,358 A | 5/1987 | Hyon |
| 4,743,256 A | 5/1988 | Brantigan |
| 4,772,287 A | 9/1988 | Ray |
| 4,834,757 A | 5/1989 | Brantigan |
| 4,904,260 A | 2/1990 | Ray |
| 4,932,969 A | 6/1990 | Frey |
| 4,950,258 A | 8/1990 | Kawai |
| 5,015,255 A | 5/1991 | Kuslich |
| 5,047,055 A | 9/1991 | Bao |
| 5,059,193 A | 10/1991 | Kuslich |
| 5,100,422 A | 3/1992 | Berguer |
| 5,123,926 A | 6/1992 | Pisharodi |
| 5,147,374 A | 9/1992 | Fernandez |
| 5,171,278 A | 12/1992 | Pisharodi |
| 5,171,280 A * | 12/1992 | Baumgartner ............ 623/17.12 |
| 5,192,326 A | 3/1993 | Bao |

(Continued)

*Primary Examiner*—Eduardo C Robert
*Assistant Examiner*—David Comstock
(74) *Attorney, Agent, or Firm*—Gifford, Krass, Sprinkle, Anderson & Citkowski, P.C.

(57) ABSTRACT

A method for retaining an intra-discal material within an annulus fibrosis is described. The annulus fibrosis has a posterior annulus, an inside surface, and an opening with a lateral and a vertical dimension. A single wire and a band is provided. The single wire is made of shape-memory material and has a first compressed configuration and a second expanded configuration. The band and the single wire, which is in the first compressed configuration, is inserted through the opening in the annulus fibrosis. After insertion through the opening, the single wire expands to the second expanded configuration. The single wire and the band are positioned near the posterior annulus to rest against annulus fibrosis tissues adjacent the opening on the inside surface of the annulus fibrosis, such that the band is positioned to rest against annulus fibrosis tissues adjacent the opening, thereby preventing escape of intra-discal material through the opening.

6 Claims, 15 Drawing Sheets

U.S. PATENT DOCUMENTS

| | | |
|---|---|---|
| 5,258,043 A | 11/1993 | Stone |
| 5,304,194 A | 4/1994 | Chee |
| 5,342,394 A | 8/1994 | Matsuno |
| 5,370,660 A | 12/1994 | Weinstein |
| 5,390,683 A | 2/1995 | Pisharodi |
| 5,425,772 A | 6/1995 | Brantigan |
| 5,496,318 A | 3/1996 | Howland |
| 5,540,715 A | 7/1996 | Katsaros |
| 5,545,229 A | 8/1996 | Parsons |
| 5,562,736 A | 10/1996 | Ray |
| 5,571,189 A | 11/1996 | Kuslich |
| 5,578,034 A | 11/1996 | Estes |
| 5,645,597 A | 7/1997 | Krapiva |
| 5,674,296 A | 10/1997 | Bryan |
| 5,681,310 A | 10/1997 | Yuan |
| 5,716,416 A | 2/1998 | Lin |
| 5,800,549 A | 9/1998 | Bao |
| 5,800,550 A | 9/1998 | Sertich |
| 5,824,093 A | 10/1998 | Ray |
| 5,827,328 A | 10/1998 | Buttermann |
| 5,865,845 A | 2/1999 | Thalgott |
| 5,879,366 A | 3/1999 | Shaw |
| 5,916,225 A | 6/1999 | Kugel |
| 5,931,838 A | 8/1999 | Vito |
| 5,976,174 A | 11/1999 | Ruiz |
| 5,976,186 A | 11/1999 | Bao |
| 6,007,570 A | 12/1999 | Sharkey |
| 6,024,754 A | 2/2000 | Engelson |
| 6,039,761 A | 3/2000 | Li |
| 6,039,762 A | 3/2000 | McKay |
| 6,066,175 A | 5/2000 | Henderson |
| 6,095,149 A | 8/2000 | Sharkey |
| 6,132,465 A | 10/2000 | Ray |
| 6,143,032 A | 11/2000 | Schafer |
| 6,193,757 B1 | 2/2001 | Foley |
| 6,206,923 B1 | 3/2001 | Boyd |
| 6,224,602 B1 | 5/2001 | Hayes |
| 6,224,630 B1 | 5/2001 | Bao |
| 6,235,034 B1 | 5/2001 | Bray |
| 6,264,695 B1 | 7/2001 | Stoy |
| 6,425,919 B1 * | 7/2002 | Lambrecht ............... 623/17.16 |
| 6,488,710 B2 | 12/2002 | Besselink |
| 6,613,089 B1 | 9/2003 | Estes |
| 6,656,178 B1 | 12/2003 | Veldhuizen et al. |
| 6,660,037 B1 | 12/2003 | Husson |
| 6,712,853 B2 | 3/2004 | Kuslich |
| 6,733,531 B1 | 5/2004 | Trieu |

* cited by examiner

POSTERIOR

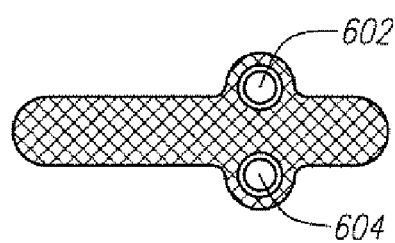
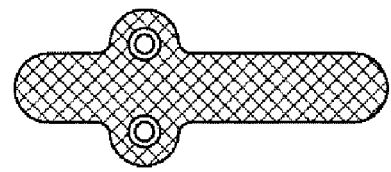
FIG. 6A          FIG. 6B
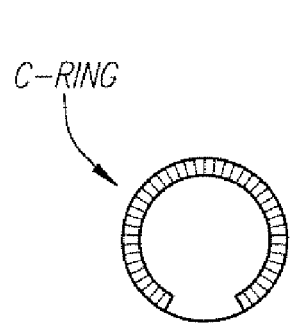
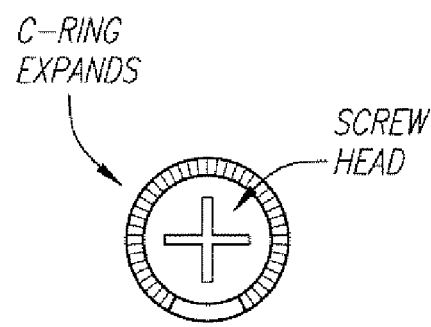
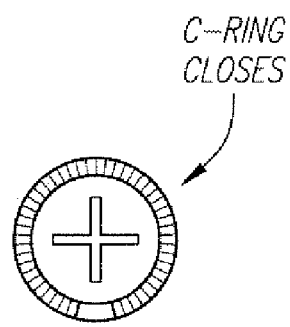
FIG. 7A          FIG. 7B          FIG. 7C

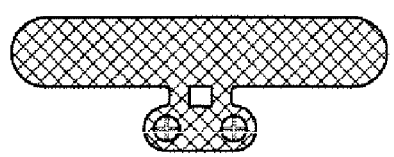
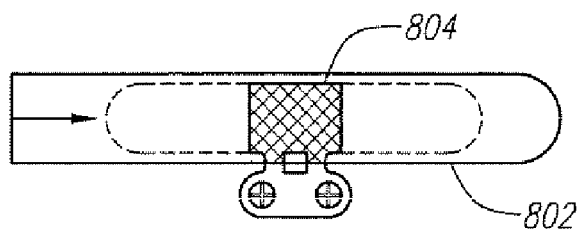
FIG. 8A　　　　　　　　FIG. 8B
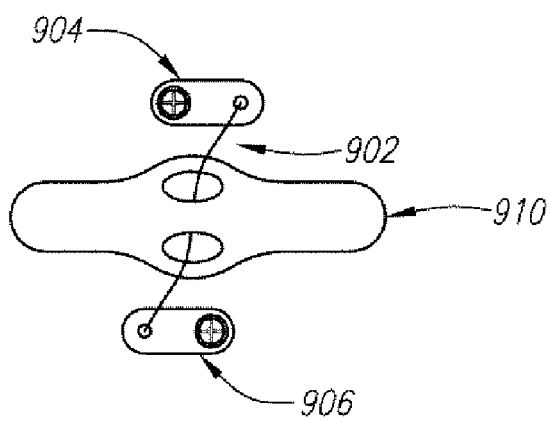
FIG. 9A
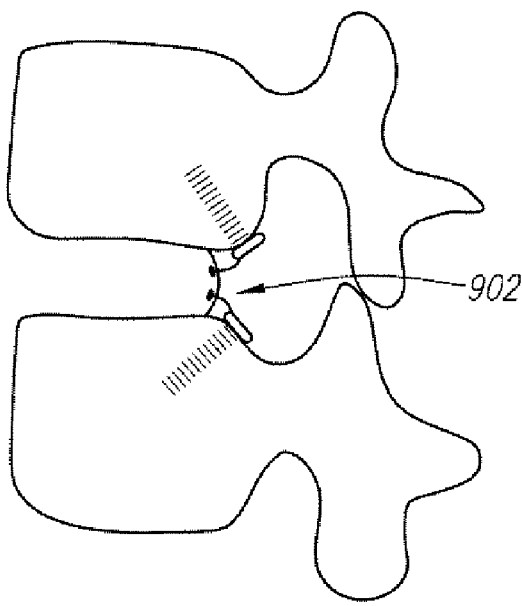
FIG. 9B

DEVICES USED TO TREAT DISC HERNIATION AND ATTACHMENT MECHANISMS THEREFORE

REFERENCE TO RELATED APPLICATIONS

This application is a continuation of U.S. patent application Ser. No. 10/185,284, filed Jun. 26, 2002, now abandoned, which is a continuation-in-part of U.S. patent application Ser. No. 09/415,382, filed Oct. 8, 1999, now issued as U.S. Pat. No. 6,419,704. This application is related to U.S. patent application Ser. Nos. 10/120,763, filed April 2002, now issued as U.S. Pat. Nos. 6,969,404 and 09/807,820, filed Apr. 19, 2001, now abandoned. The entire content of each application is incorporated herein by reference.

FIELD OF THE INVENTION

This invention relates generally to devices used to treat disc herniation and, in particular, to attachment methods and apparatus therefore.

BACKGROUND OF THE INVENTION

Several hundred thousand patients undergo disc operations each year. Approximately five percent of these patients will suffer recurrent disc herniation, which results from a void or defect which remains in the outer layer (annulus fibrosis) of the disc after surgery involving partial discectomy.

Reference is made to FIG. 1A, an axial cross-section of a normal disc, including the "safe zones.". The nucleus pulposus 102 is entirely surrounded by the annulus fibrosis 104 in the case of healthy anatomy. Also shown in this cross section is the relative location of the nerves 106. FIG. 1B illustrates the case of the herniated disc, wherein a portion of the nucleus pulposus has ruptured through a defect in the annulus fibrosis, resulting in a pinched nerve 110. This results in pain and further complications, in many cases.

FIG. 1C illustrates the post-operative anatomy following partial discectomy, wherein a space 120 remains adjacent a hole or defect in the annulus fibrosis following removal of the disc material. The hole 122 acts as a pathway for additional material to protrude into the nerve, resulting in the recurrence of the herniation. Since thousands of patients each year require surgery to treat this condition, with substantial implications in terms of the cost of medical treatment and human suffering, any solution to this problem would welcomed by the medical community.

As disclosed and described in the related applications referenced above and incorporated herein by reference, devices used to prevent recurrent disc herniations may be attached in numerous ways, depending upon the extent of the defect, overall patient physiology, and other considerations. For example, such devices may attach to the vertebral endplates, to the annulus fibrosis, to the nucleous pulposus, to the pedicle facet, or other posterior aspect of the vertebrae. Under these more generalized approaches, numerous other more targeted procedures may be used, particularly with respect to annulus fibrosis attachment. For example, devices may be attached to the inner portion of the annulus, including the inner surface, or to the outer surface. With respect to external attachment, positioning typically considers the "safe zone" so as to avoid the great vessels anteriorally, and the nerve or spinal posteriorally.

Given the great variance in defect type, as well as the variability in anatomical structure, particularly at the different vertebral levels, additional methods and apparatus used to maintain devices for preventing recurrent disc herniation are always welcome, particularly if such components, instruments and procedures lend additional stability or longevity.

SUMMARY OF THE INVENTION

This invention resides in apparatus for preventing the escape of natural, artificial, or therapeutic material through a defect in the annulus fibrosis, with particular emphasis on attachment mechanisms for such apparatus. The preferred embodiment resides a device having height and lateral extensions, the width of the lateral extensions being substantially greater than the width of the defect in the annulus, such that when the device is introduced into the disc through the defect, the extensions overlap with the annulus fibrosis on both side of the defect from the inside, thereby preventing the escape of the natural, artificial, or therapeutic material.

In one preferred embodiment, the device is in the form of an elongate band. In an alternative embodiment, the device is in the form of a plate having upper or lower extensions for respective fastening to upper or lower vertebra. The extensions are preferably fastened with screws, with the apparatus further including an anti-backout mechanism in the form of a C-ring positioned around each screw or a mobile link member from the plate to the screw.

The lateral extensions may be integral to the device or, alternatively, may be separate and outwardly biased, as with springs. The apparatus may further include an intradiscal ring to which the device attaches. The intradiscal ring may additionally includes one or more anti-rotation projections. As yet a further option, the device may be hinged, and may include mesh, teeth, or other material to further prevent the escape of the natural, artificial, or therapeutic material.

BRIEF DESCRIPTION OF THE DRAWINGS

FIG. 5J shows a first band inserted into the disc, followed by a second band;

FIG. 6A is a detailed view of disc herniation prevention plate according to the invention;

FIG. 6B is a detailed drawing of an alternative plate;

FIG. 7A is a drawing of a screw hole illustrating the use of a C-ring to prevent backout;

FIG. 7B shows the structure of FIG. 7A with the screw progressing past the C-ring;

FIG. 7C shows the screw passing through the ring, thus locking the structure in position;

FIG. 8A is a drawing of a further alternative herniation prevention plate according to the invention;

FIG. 8B illustrates the use of the plate 8A in position within the disc;

FIG. 9A illustrates an alternative mechanism to prevent screw backout;

FIG. 9B illustrates the components of FIG. 9A from a lateral perspective;

DETAILED DESCRIPTION OF THE INVENTION

As discussed above, this invention resides in various alternative components and procedures used to treat disc herniation and recurrent disc herniation. Depending upon the precise mechanism and procedural protocol, the devices may be introduced anteriorally, posteriorally, percutaneously or laparoscopically.

FIGS. 3 and 4 refer an to embodiment of the invention wherein a band is placed around the inside of the disc. This may be placed percutaneously or endoscopically utilizing steerable catheters, spinal endoscopes, and other endoscopic instruments currently in use by surgeons. Fluoroscopic guidance may advantageously be used. A single wire, band or other structure, which may or may not include a shape-memory material, is introduced into the disc space. Depending upon the circumstances, a wider band may be slid over a previously introduced smaller wire.

Minimally invasive procedures of this kind may be used on patients whose herniation has healed naturally. The procedure may also be used on patients with bulging discs, or whoever has a relatively high risk of suffering recurrent herniation. Unlike larger devices, these embodiments do not require a large incision through the annulus, as they may be inserted through a puncture just large enough to insert the band. Indeed, the fibers of the annulus may be bluntly separated as opposed to being cut.

Figure 1A:
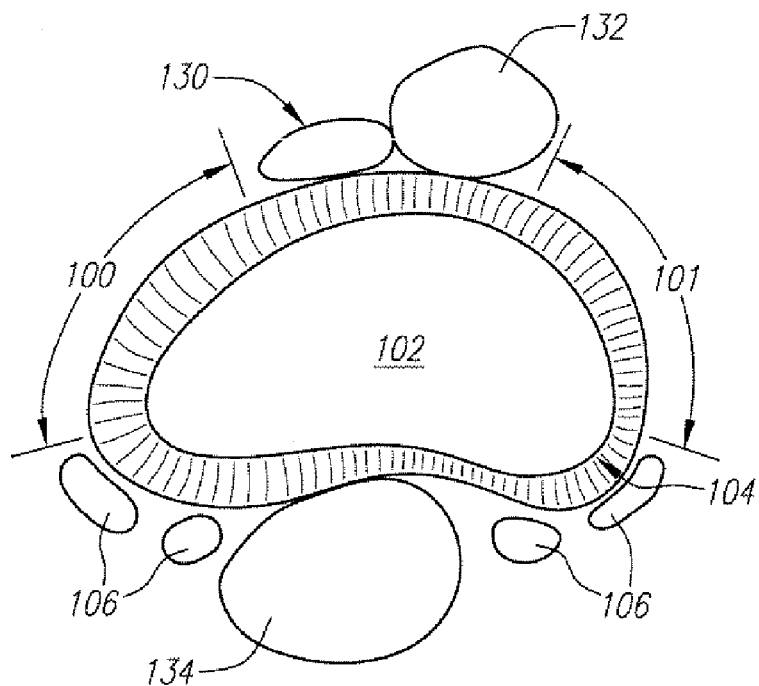
FIG. 1A is an axial cross-section of a disc and surrounding structures, illustrating the "safe zones"
Figure 1B:
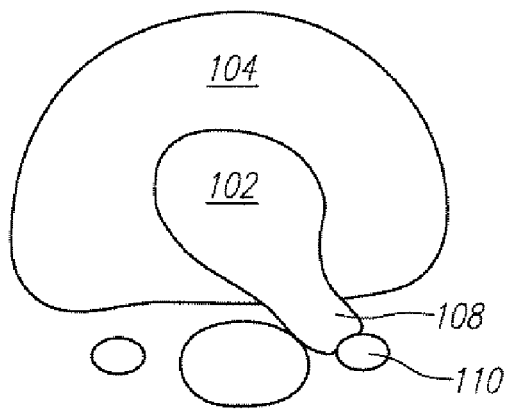
FIG. 1B illustrates the case of the herniated disc, wherein a portion of the nucleus pulposus has ruptured through a defect in the annulus fibrosis, resulting in a pinched nerve.
Figure 1C:
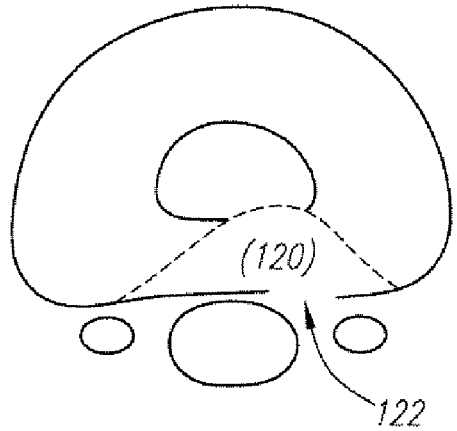
FIG. 1C illustrates the post-operative anatomy following partial discectomy, wherein a space remains adjacent a hole or defect in the annulus fibrosis following removal of the disc material.
Figure 2:
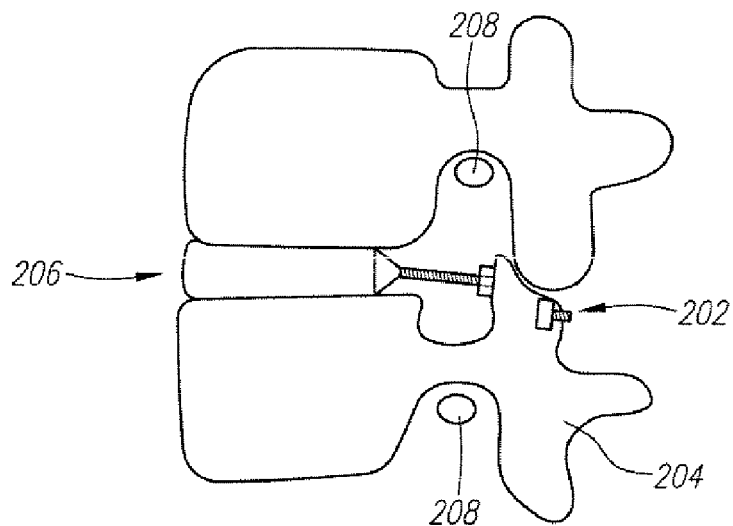
FIG. 2 is a lateral view of the spine, showing the way in which a device may be attached to the superior facet of an inferior vertebra to maintain a posterior herniation.
Figure 3A:
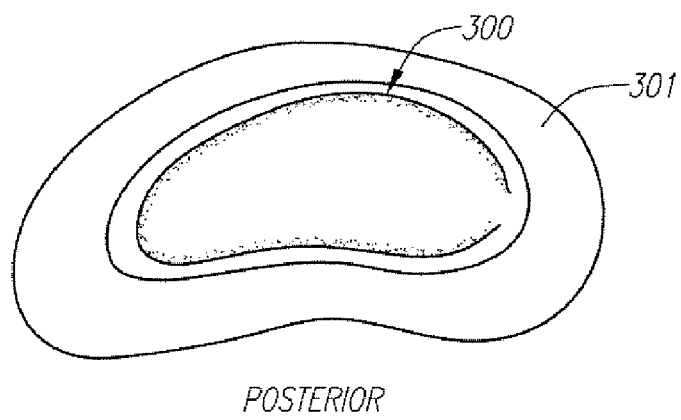
FIG. 3A is a drawing of a band according to the invention placed around the inside of the disc.
Figure 3B:
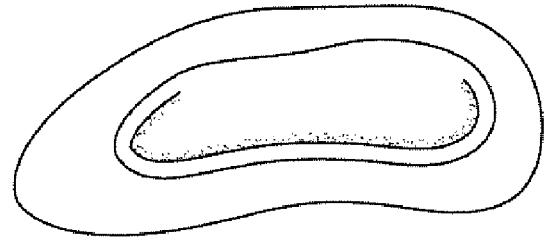
FIG. 3B is a drawing which illustrates an alternative placement of a disc band.

FIG. 3A is a drawing of a band according to the invention placed around the inside of the disc. FIG. 3B is a drawing which illustrates an alternative placement of a disc band. In the preferred embodiment, this disc bands are placed percutaneously. However, the bands may be inserted through a hole in the annulus using more traditional surgical methods, preferably the aid of an endoscope and/or endoscopic instruments.

Figure 3C:
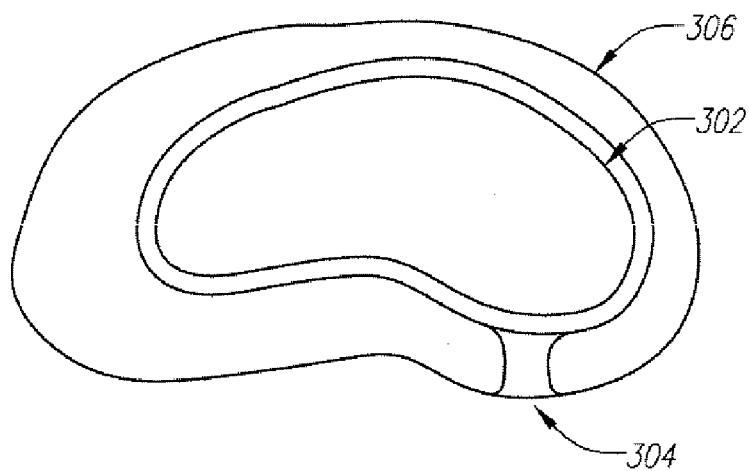
FIG. 3C illustrates the way in which a wire may be introduced through a hole in the annulus.

For example, FIG. 3C illustrates the way in which a wire 302 may be introduced through a hole 304 in the annulus 306. Once placed, the wire may serve as a guide to slide over a wider band which, in combination, would serve to block nucleus tissue from extruding through the hole. Preferably, the band would cover the entire wire or just a portion of the wire adjacent to the hole in the annulus. The wire may also be cut to facilitate insertion of the band over the wire, or the ends of the wire may be coupled after the band is placed. Multiple bands that stack upon one another may also be used with or without a wire.

Figure 3D:
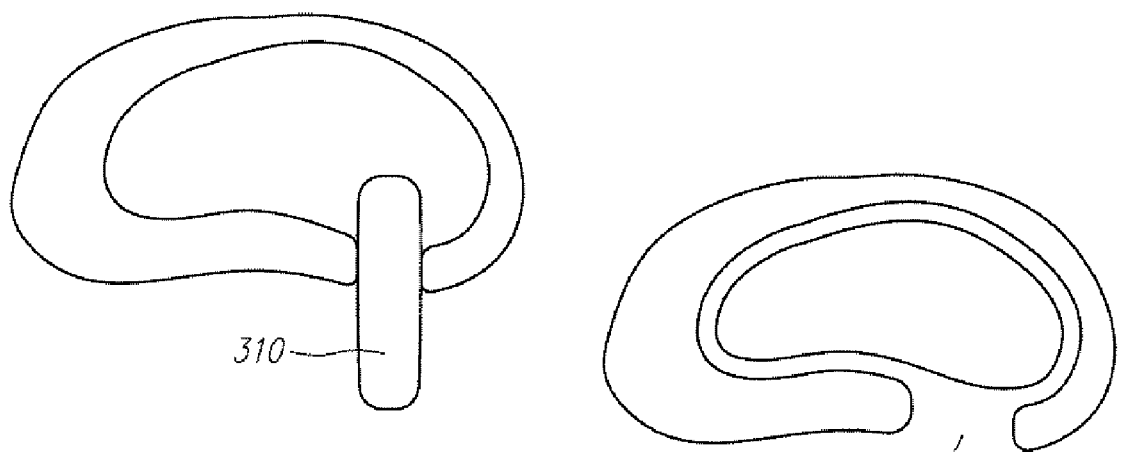
FIG. 3D is a sectional drawing which shows the introduction of a shape-memory band being inserted through a hole in the annulus.
Figure 3E:
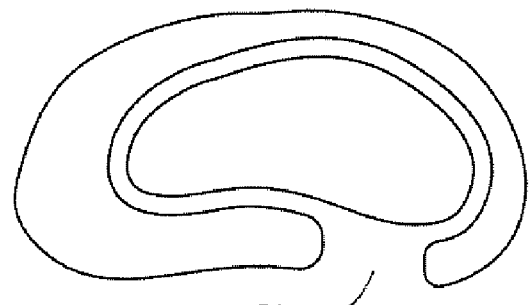
FIG. 3E is a drawing which shows the band of FIG. 3D in an expanded state operative to occlude the hole.

The wire may be of a shape-memory material, permitting insertion with a first, compressed configuration, followed by a natural expansion. Either a single wire or band may be used, or pieces may be inserted and assembled in situ. FIG. 3D is a sectional drawing which shows the introduction of a shape-memory band 310 being inserted through a hole in the annulus. FIG. 3E is a drawing which shows the band of FIG. 3D in an expanded state operative to occlude the hole 304.

Figure 3F:
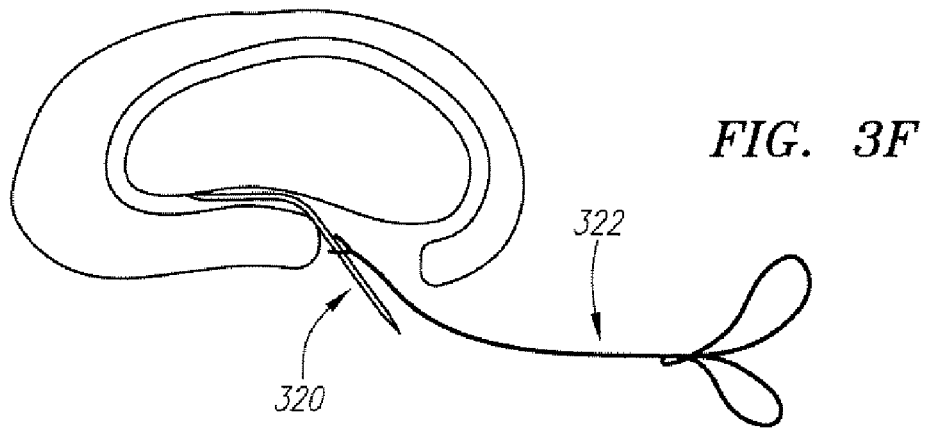
FIG. 3F is a drawing which shows the optional insertion of a band over or onto a wire of the type shown in FIGS. 3C-3E.
Figure 3G:
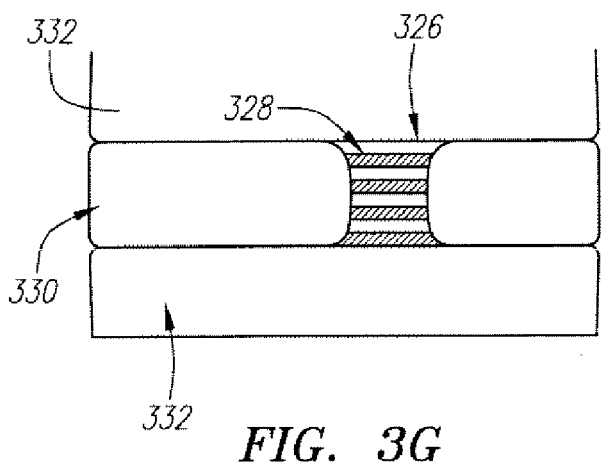
FIG. 3G is a side-view drawing illustrating how multiple wires may be used to occlude the hole in the annulus between adjacent vertebrae.
Figure 3H:
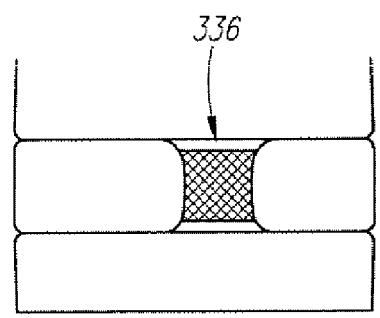
FIG. 3H illustrates the use of a single larger band placed over a wire or wires according to the present invention.

FIG. 3F is a drawing which shows the optional insertion of a band over or onto a wire of the type shown in FIGS. 3C-3E. The band is indicated at 320, with 320 referring to an instrument used to push the band along the wire or wires. FIG. 3G is a side-view drawing illustrating how multiple wires 326 may be used to occlude the hole 328 in the annulus 330 between adjacent vertebrae 332. FIG. 3H illustrates the use of a single larger band 336 placed over a wire or wires according to the invention.

Figure 3I:
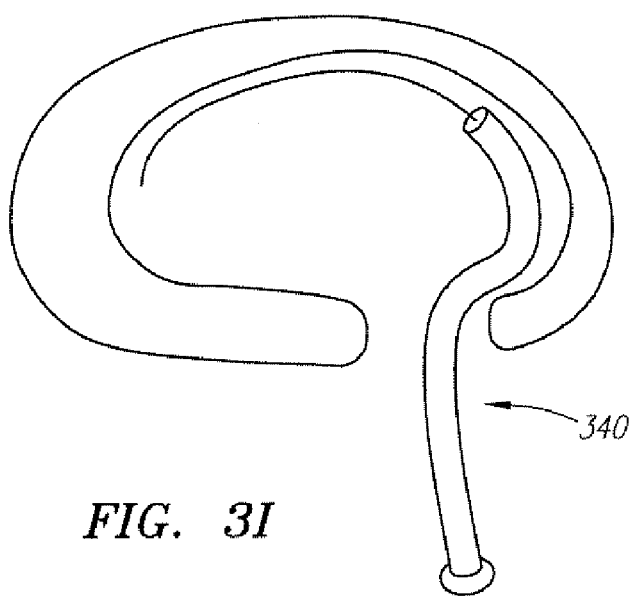
FIG. 3I shows the way in which a guide may be used to help direct bands into the disc.
Figure 3J:
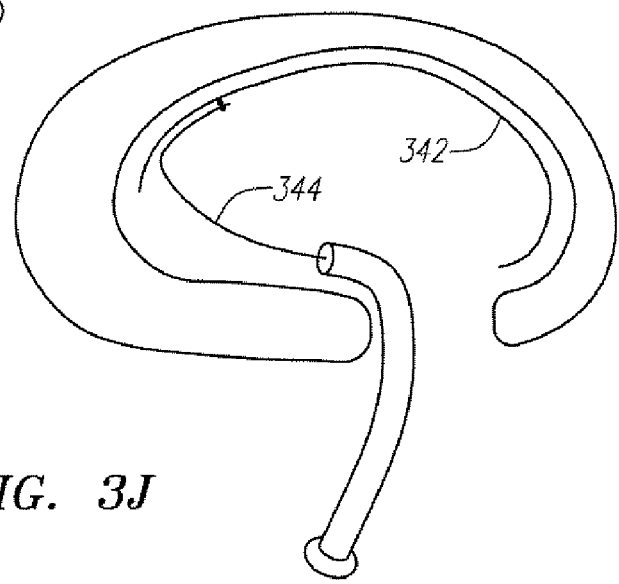
FIG. 3K illustrates the use of a separate instrument used to slide the band.
FIG. 3L is a drawing which shows how the two bands may be locked to form a complete unit to occlude a defect.
FIG. 3M is a cross-section of one embodiment of a band according to the invention.
Figure 3K:
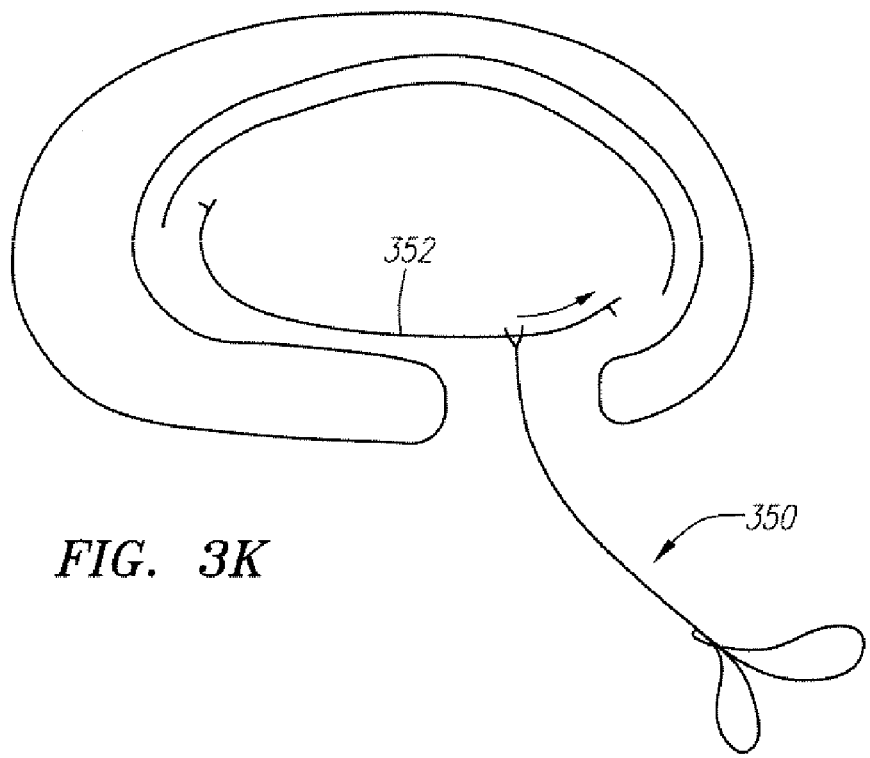
Figure 3L:
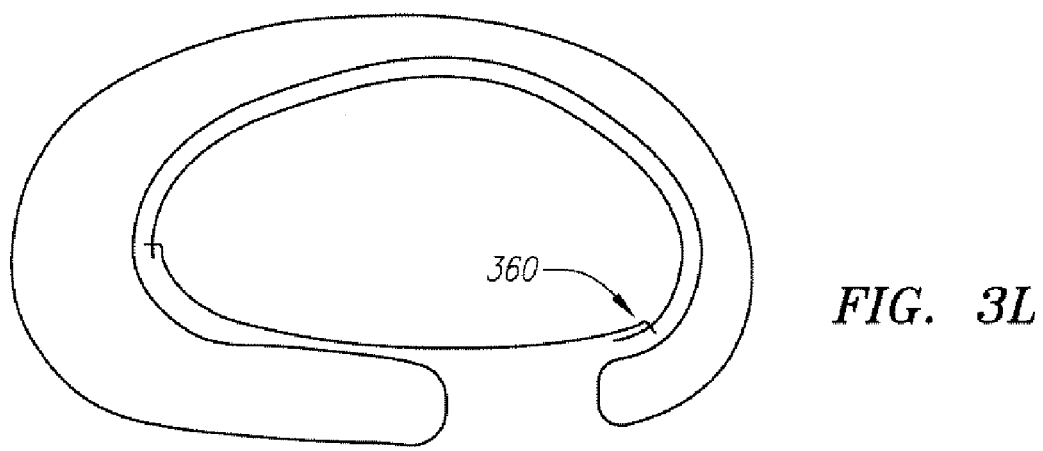
Figure 3M:
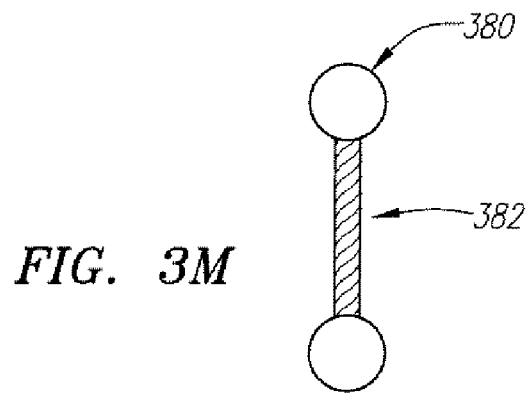

FIG. 3I is a drawing which shows the way in which a guide 340 may be used to help direct bands into the disc. FIG. 3J, a first band 342 has been inserted into the disc, followed by a second band 344. FIG. 3K illustrates the use of a separate instrument 350 used to slide the band 352. FIG. 3L is a drawing which shows how the two bands may be locked at 360 to form a complete unit to occlude a defect. FIG. 3M is a cross-section of one embodiment of a band according to the invention, wherein a wire 380 is attached to a flexible mesh or material 382 to allow motion of the spine without impingement of the band.

Figure 4A:
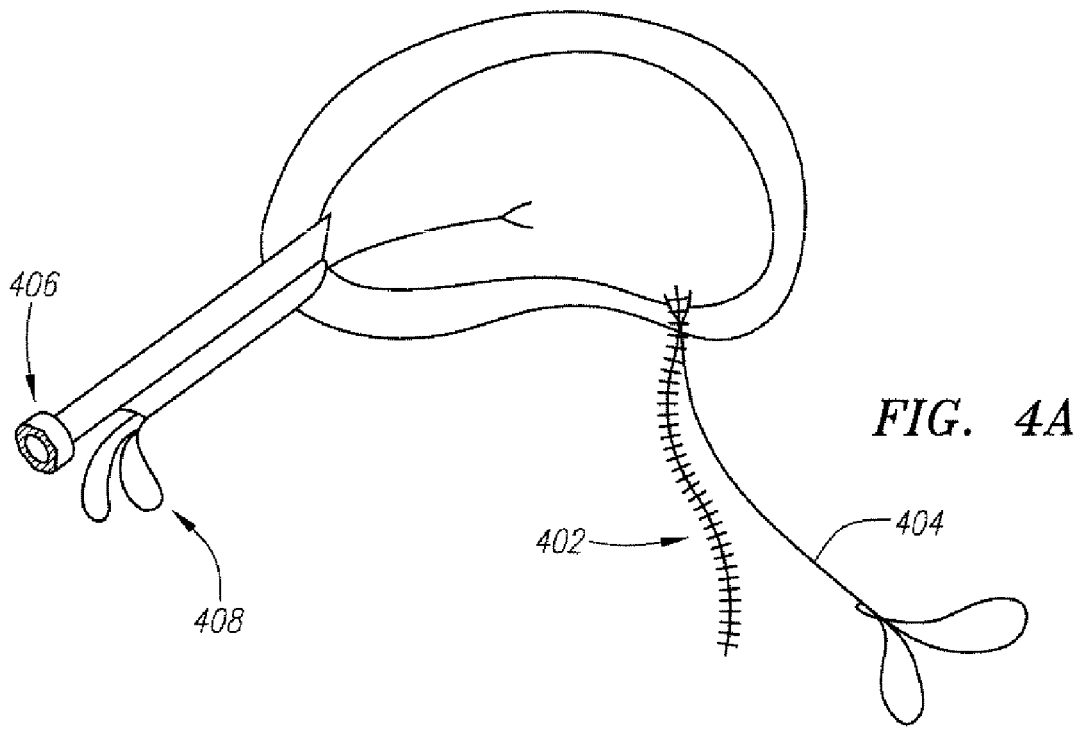
FIG. 4A begins a series of drawings which shows an endoscopic placement of bands such as those shown in FIGS. 5A and 5B.
Figure 4B:
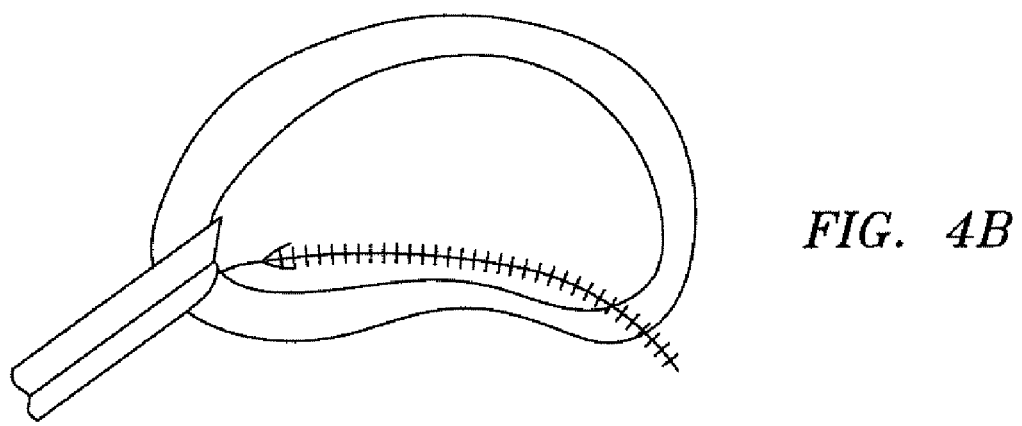
FIG. 4B shows the band entering into the annulus.
Figure 4C:
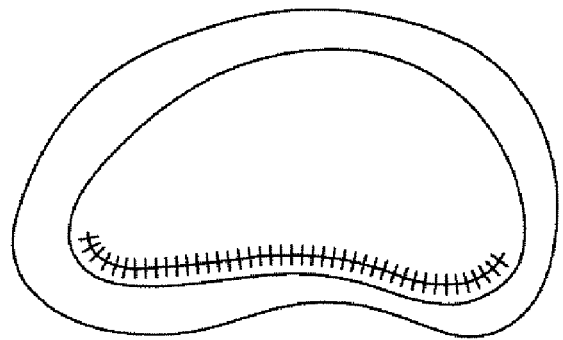
FIG. 4C shows how the band may be stapled or sutured to the inside of the annulus.
Figure 4D:
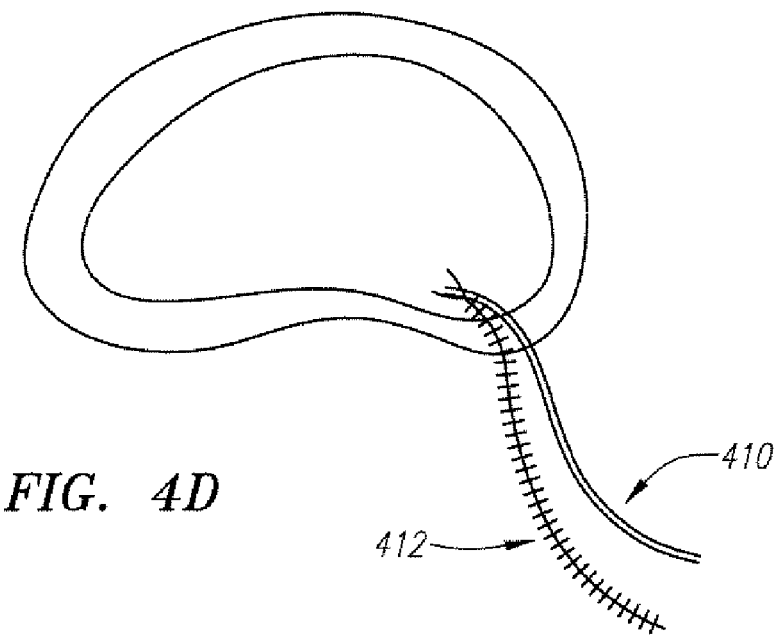
FIG. 4D illustrates the use of a steerable catheter in conjunction with an annulus band.
Figure 4E:
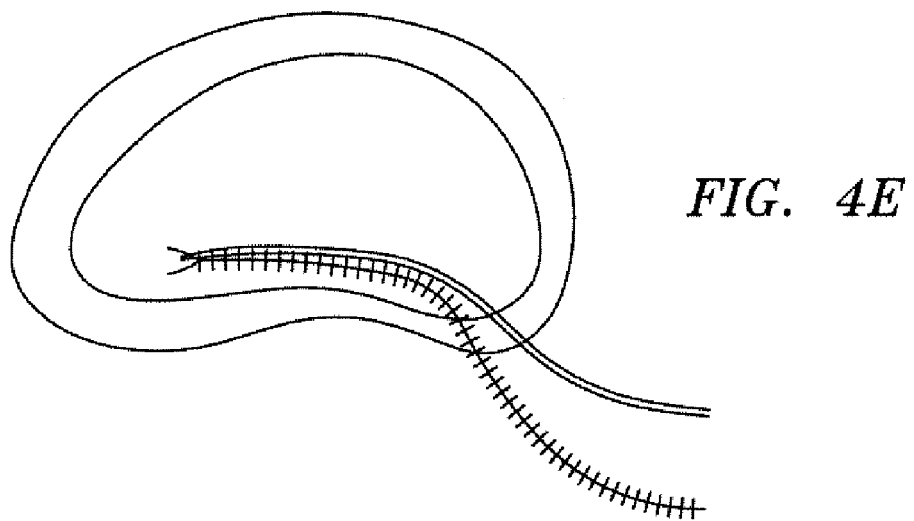
FIG. 4E illustrates a further progression of the catheter and band.
Figure 4F:
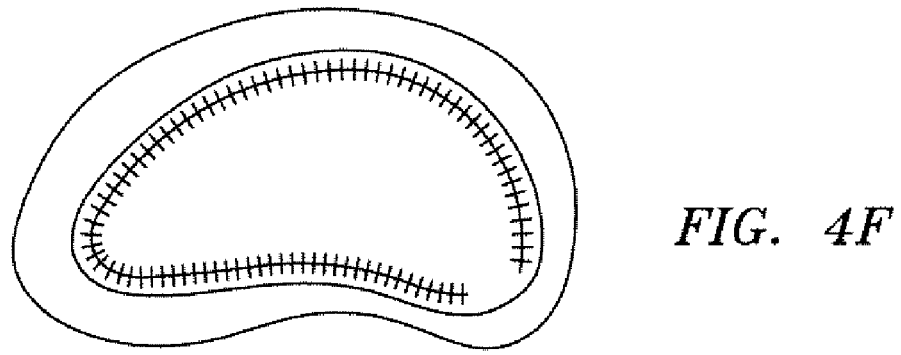
FIG. 4F shows the band in place.

FIG. 4A begins a series of drawings which shows an endoscopic placement of bands such as those shown in FIGS. 3A and 3B. FIG. 4B shows the band entering into the annulus. FIG. 4C shows how the band may be stapled or sutured to the inside of the annulus. FIG. 4D illustrates the use of a steerable catheter in conjunction with an annulus band. FIG. 4E illustrates a further progression of the catheter and band. FIG. 4F shows the band in place.

Figure 5A:
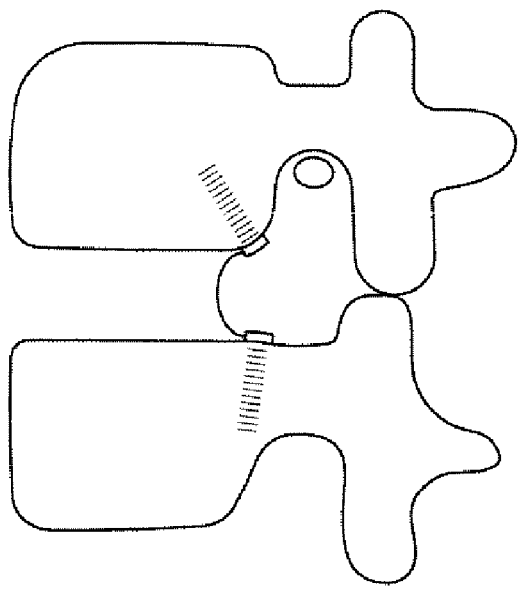
FIG. 5A is a lateral view illustrating an alternative containment device according to the invention.
Figure 5B:
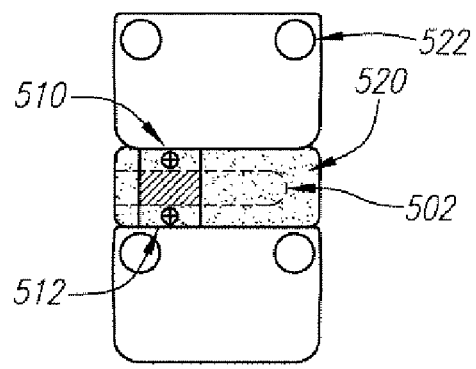
FIG. 5B is a posterior view with the lamanae and facets removed.
Figure 5C:
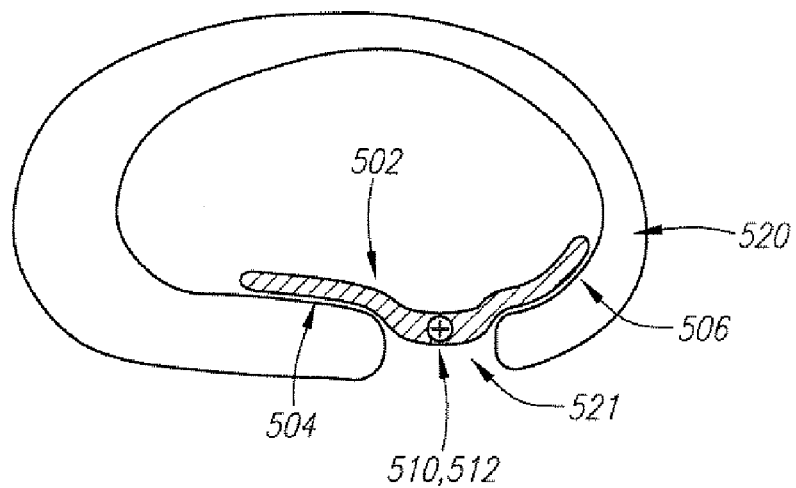
FIG. 5C is a cross-section of the device shown in FIGS. 5A and 5B.

The devices according to this invention used to retain the nucleus may also be used to contain intradiscal devices, including artificial disc replacements. The anchor members shown in particular in FIGS. 9C, 15D and 24 of U.S. patent application Ser. No. 09/807,820, for example, incorporated herein by reference, may include a mechanism that prevents the screws from backing out of the device. For example, a C-ring that snaps closed over a screw head after the head passes through the head passes through C ring may be used to prevent the screw from loosening and backing out, which could result in the compression of a nerve and the need for additional surgery. I have described various other screw backout features, including device 410 in FIG. 4 of U.S. patent application Ser. No. 09/415,382. The preferred embodiment includes two or more screws to prevent rotation. FIG. 5A is a lateral view illustrating an alternative containment device according to the invention. FIG. 5B is a posterior view with the lamanae and facets removed. FIG. 5C is a cross-section of the device shown in FIGS. 5A and 5B. The device 502 includes lateral extensions 504 and 506 that project behind the annulus, as perhaps best seen in FIG. 5C. The device is held in place with screws 510 and 512, which are anchored to the upper and lower vertebrae, as best seen in FIG. 5A.

FIG. 6A is a detailed view of disc herniation prevention plate according to the invention. FIG. 6B is a detailed drawing of an alternative plate. Such devices may have different sizes and shapes to suit different patient physiologies. For example, the device may have asymmetric lateral extensions on the left or right side, or such extensions may be symmetric, depending upon the defect and other considerations. Such devices may be made with any suitable materials, including shape-memory materials, enabling a collapsed state of insertion, followed by an expanded state for inclusion of the defect.

The screws preferably extend through the endplate of the vertebrae, though they may also be placed into the pedicle, lamina or facet, depending upon the shape of the plate and other considerations.

The screw holes in these devices may include a C-ring to prevent backout. FIG. 7A is a drawing of a screw hole illustrating the use of a C-ring to prevent backout. FIG. 7B shows the structure of FIG. 7A with the screw progressing past the C-ring. FIG. 7C shows the screw passing through the ring, thus locking the structure in position. By way of a partial summation the retaining mechanism thus far described and the descriptions to follow preferably include a locking mechanism for the screws to prevent backout. The extension of the device extends behind the intact annulus, thereby resisting extrusion compared to devices which are entirely external, with the screws anchoring the device to prevent migration. These devices preferably collapse for entry through a hole in the annulus, then return to a desired shape to assume the blocking function. As such, the longer lateral extensions, or both extensions, may be slid behind the annulus with or without shape memory properties. In the preferred embodiments, these devices are flexible enough to allow spinal motion, that is, they are sufficiently flexible to bend and retain their normal shape with spinal flexion and extension. FIG. 5A is a drawing of a further alternative herniation prevention plate according to the invention. FIG. 8B illustrates the use of the plate 8A in position within the disc.

FIG. 9A illustrates an alternative mechanism to prevent screw backout. FIG. 9B illustrates the components of FIG. 9A from a lateral perspective, which best illustrates the use of a mobile link member 902. This mobile link member allows additional movement of the device with spinal movement while, at the same time, protects the screws from stresses that might occur through such movements. While the screws maintain the position of the device overall, the screen-like component holds the nucleus and intradiscal device in position and experiences a majority of the extrusion forces. The intact annulus adjacent to the annulus hole resists most of the extrusion force on the screen component, however.

Figure 10A:
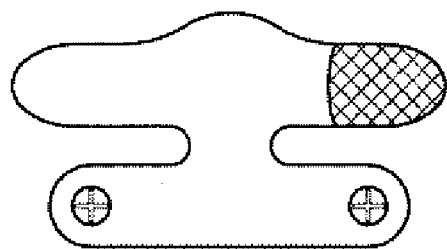
FIG. 10A is a drawing of a plate including a spring-biased extension in an extended state.
Figure 10B:
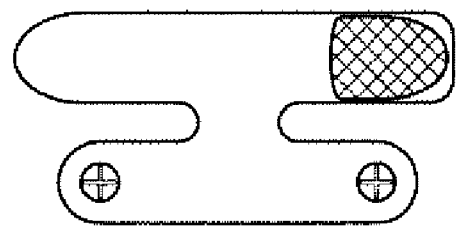
FIG. 10B illustrates the plate of FIG. 10A in a contracted state.
Figure 11A:
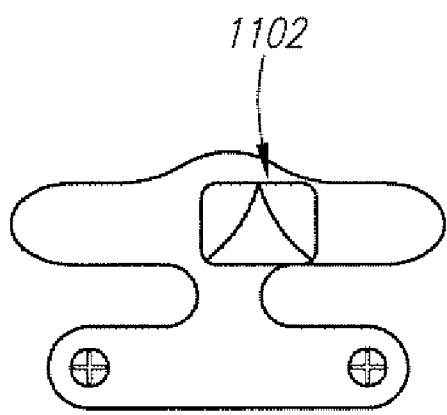
FIG. 11A is a cut-away view of the device in the state of FIG. 10A.
Figure 11B:
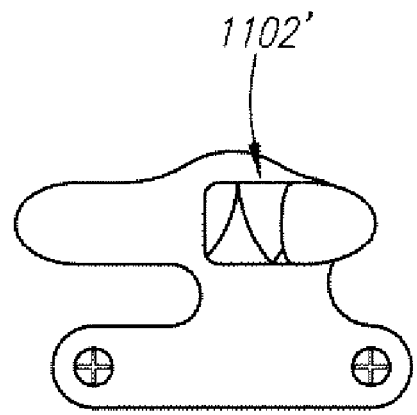
FIG. 11B is a cut-away view of the device of FIG. 10B, illustrating the spring being compressed.

FIGS. 10-11 illustrate the use of an alternative embodiment of the invention wherein the lateral extensions are spring-loaded as opposed to shape-memory in nature. FIG. 10A is a drawing of a plate including a spring-biased extension in an extended state, FIG. 10B illustrates the plate of FIG. 10A in a contracted state. FIG. 11A is a cut-away view of the device in the state of FIG. 10A. FIG. 11B is a cut-away view of the device of FIG. 10B, illustrating the spring being compressed.

Figure 12A:
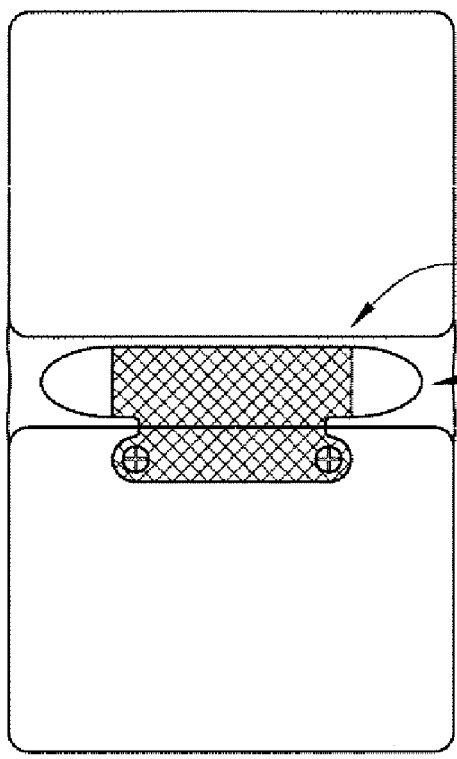
FIG. 12A illustrates a plate according to the invention incorporating an opposing pair of lateral extensions to cover the disc space more securely.
Figure 12B:
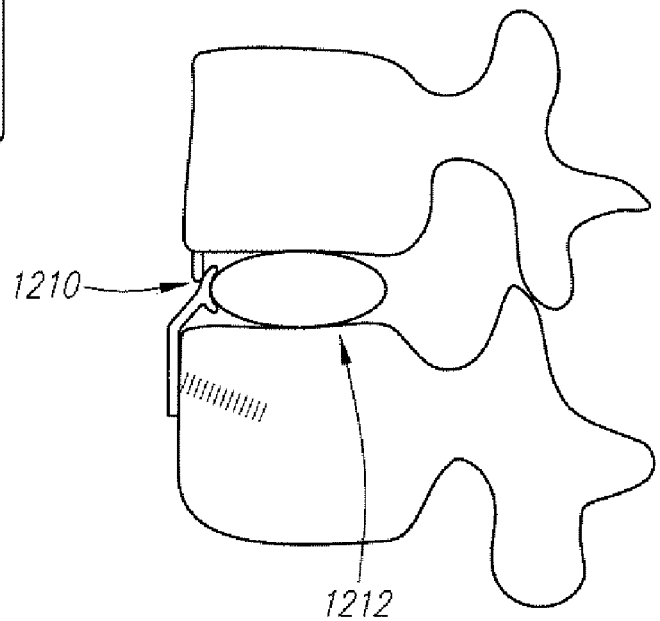
FIG. 12B is a lateral view showing the lateral extension disposed behind the patient's remaining annulus.
Figure 12C:
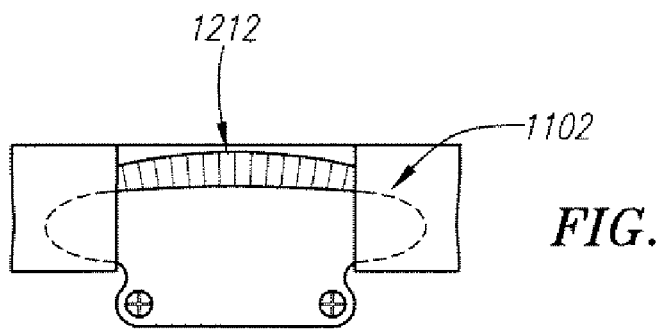
FIG. 12C is a close-up view of the device of FIGS. 12A and 12B.

FIG. 12A illustrates a plate according to the invention incorporating an opposing pair of lateral extensions to cover the disc space more securely. FIG. 12B is a lateral view showing the lateral extension disposed behind the patient's remaining annulus. FIG. 12C is a close-up view of the device of FIGS. 12A and 12B.

Figure 13A:
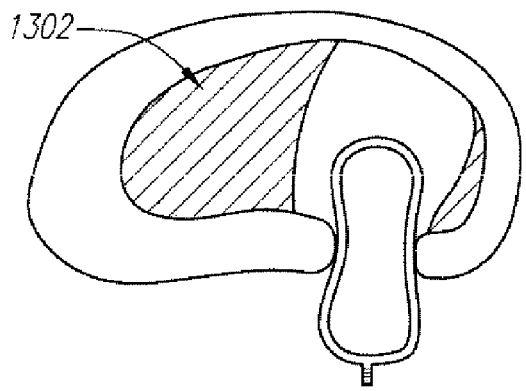
FIG. 13A begins a series of drawings illustrating an alternative embodiment according to the invention used to prevent recurrent disc herniation.
Figure 13B:
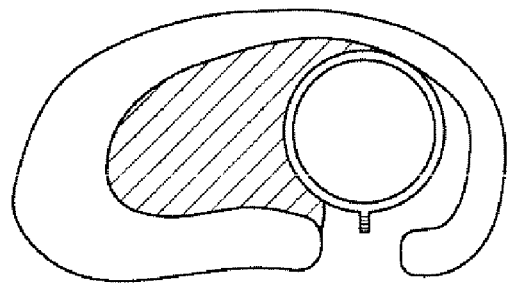
FIG. 13B illustrates the device of FIG. 13A in place within the disc space.
Figure 13C:
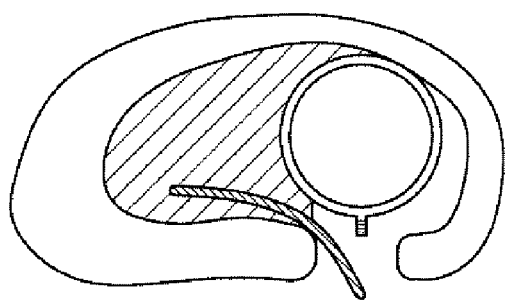
FIG. 13C illustrates the introduction of a locking member.
Figure 13D:
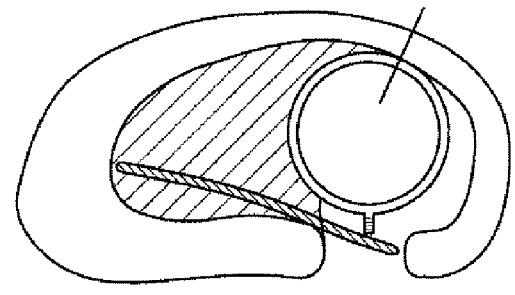
FIG. 13D shows the locking member positioned within the disc space.
Figure 13E:
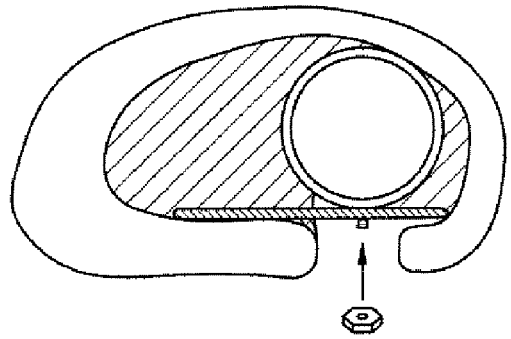
FIG. 13E shows the addition of a locking nut.
Figure 13F:
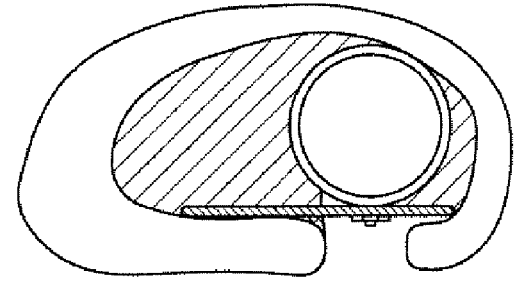
FIG. 13F shows the ring-shaped device now locked to the occluding plate.
Figure 14:
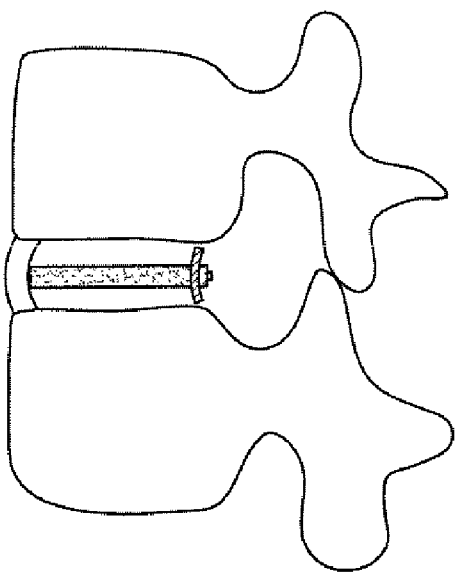
FIG. 14 shows how the devices of FIG. 13 may be provided in various sizes to suit a patient's anatomy.

FIG. 13A begins a series of drawings illustrating an alternative embodiment according to the invention used to prevent recurrent disc herniation. FIG. 13B illustrates the device of FIG. 13A in place within the disc space. FIG. 13C illustrates the introduction of a locking member. FIG. 13D shows the locking member positioned within the disc space. FIG. 13E shows the addition of a locking nut, FIG. 13F shows the ring-shaped device now locked to the occluding plate. FIG.

14 shows how the devices of FIG. 13 may be provided in various sizes to suit a patient's anatomy.

Figure 15B:
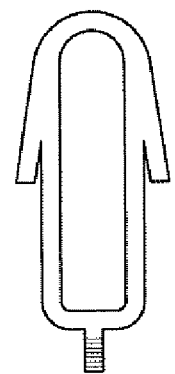
FIG. 15B shows the device of FIG. 15A in a collapsed state for insertion.
Figure 15A:
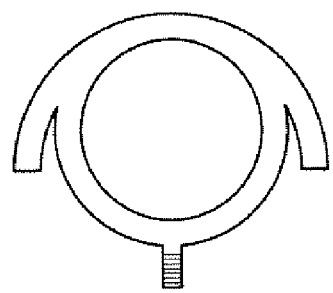
FIG. 15A illustrates yet a further embodiment of a device similar to that shown in FIGS. 13 and 14, including an anti-rotation feature.

FIGS. 15A and 15B show a further alternative embodiment of the invention making advantageous use of anti-rotation projections. FIG. 15A shows a ring-like component in an expanded state, whereas FIG. 15B shows the device collapsed for insertion. As described above with respect to other embodiments disclosed herein, such a ring-like component have a spring-like or shape-memory capability to alternate between the expanded and collapsed state. The posterior damper component also needs to be flexible enough to allow spinal extension. At the same time, however, the damper unit must retain its extended shape during flexion so as to block disc material.

Figure 16:
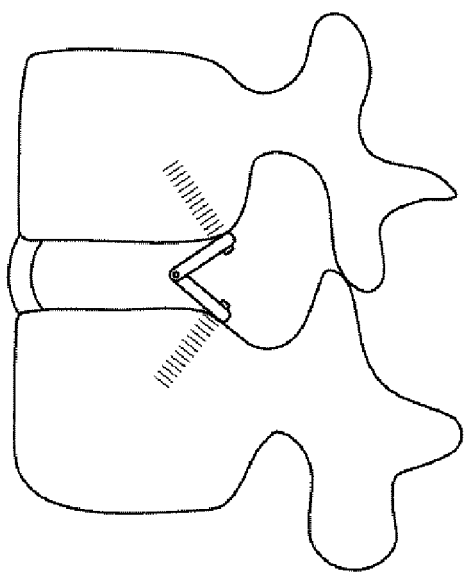
FIG. 16 is a lateral view of a different embodiment incorporating a single hinge.
Figure 17:
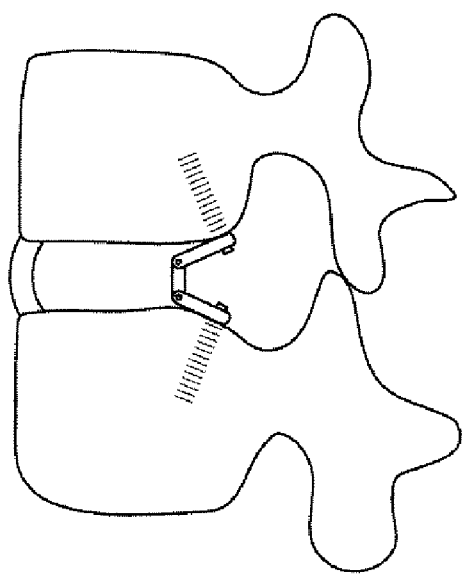
FIG. 17 is yet a different alternative embodiment of the device incorporating a plurality of hinges.
Figure 18A:
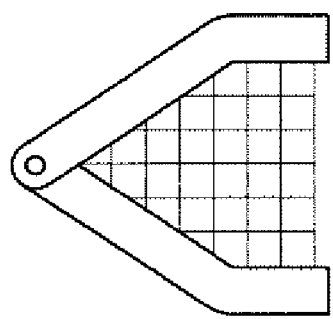
FIG. 18A shows the way in which a mesh or interdigitating teeth may be used to prevent migration of the disc material.
Figure 19A:
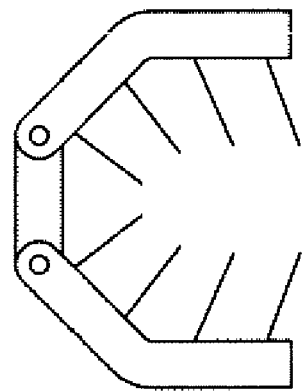
FIG. 19A shows the use of a multiple-hinge device in an extended state incorporating a mesh or interdigitating teeth.
Figure 18B:
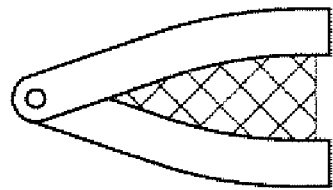
FIG. 18B shows the single-hinge device of FIG. 18A in a flexed, as opposed to extended, state.
Figure 19B:
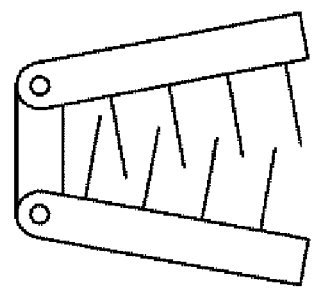
FIG. 19B shows the device of FIG. 19A in a flexed state.

FIG. 16 is a lateral view of a different embodiment incorporating a single hinge. FIG. 17 is yet a different alternative embodiment of the device incorporating a plurality of hinges. The ends of the plate may be covered with mesh, interdigitating teeth, and so forth to prevent migration of the material around the ends of the plate. FIG. 18A shows the way in which a mesh or interdigitating teeth may be used to prevent migration of the disc material. FIG. 18B shows the single-hinge device of FIG. 18A in a flexed, as opposed to extended, state. FIG. 19A shows the use of a multiple-hinge device in an extended state incorporating a mesh or interdigitating teeth. FIG. 19B shows the device of FIG. 19A in a flexed state. Preferably, the screw holes will include a mechanism to prevent backout. In addition, the component of the device that contains the screw or screws may contain a mobile link to the screen-like material. The mobile link, described above, allows additional movement of the device with spinal movement while helping to protect the screws from stresses associated with normal spinal movements.

What is claimed is:

1. A method for retaining an intra-discal material within an annulus fibrosis having a posterior annulus, an inside surface, and an opening, the opening having a lateral and a vertical dimension, comprising the steps of:
   providing a single wire and a band separate from the wire, the single wire comprising shape-memory material and having a first compressed configuration and a second expanded configuration;
   inserting the single wire in the first compressed configuration and the band through the opening in the annulus fibrosis, wherein the single wire expands to the second expanded configuration after insertion through the opening; and
   positioning the single wire and the band near the posterior annulus to rest against annulus fibrosis tissues adjacent the opening on the inside surface of the annulus fibrosis, wherein the band covers at least a portion of the single wire that is positioned to rest against annulus fibrosis tissues adjacent the opening on the inside surface of the annulus fibrosis, thereby preventing escape of intra-discal material through the opening.

2. The method of claim 1, wherein the band is a mesh.

3. The method of claim 1, wherein the band covers a portion of the single wire.

4. The method of claim 1, wherein the band covers an entire length of the single wire.

5. The method of claim 1, further comprising the step of sliding the band over the single wire after the single wire is inserted through the opening in the annulus fibrosis.

6. The method of claim 1, wherein the band is attached to the single wire.

* * * * *

UNITED STATES PATENT AND TRADEMARK OFFICE
CERTIFICATE OF CORRECTION

| | | |
|---|---|---|
| PATENT NO. | : 7,857,855 B2 | Page 1 of 1 |
| APPLICATION NO. | : 12/122612 | |
| DATED | : December 28, 2010 | |
| INVENTOR(S) | : Bret A. Ferree | |

It is certified that error appears in the above-identified patent and that said Letters Patent is hereby corrected as shown below:

Column 1, line 13: Replace "Nos." with --No.--
Column 3, line 3: Replace "5J" with --3J--
Column 3, line 12: Replace "5A" with --3A--
Column 3, line 13: Replace "5B" with --3B--
Column 6, line 29: Replace "5A" with --8A--

Signed and Sealed this

Nineteenth Day of April, 2011

David J. Kappos
*Director of the United States Patent and Trademark Office*